United States Patent [19]

Thompson

[11] 4,239,039
[45] Dec. 16, 1980

[54] DUAL CONTROL VALVE FOR POSITIVE PRESSURE ARTIFICIAL RESPIRATION APPARATUS

[76] Inventor: Harris A. Thompson, 175 Bellevue Dr., Boulder, Colo. 80302

[21] Appl. No.: 15,784

[22] Filed: Feb. 28, 1979

[51] Int. Cl.³ .......................................... A61M 16/00
[52] U.S. Cl. ........................... 128/205.24; 128/204.18
[58] Field of Search ................... 128/145.5–145.8, 128/28, 30, 30.2, 276, 273, 274, 204.18, 204.21, 204.25, 205.12, 205.19, 205.24; 415/125; 137/865, 870, 862

[56] References Cited

U.S. PATENT DOCUMENTS

| | | | |
|---|---|---|---|
| 2,770,231 | 11/1956 | Falk | 128/145.6 |
| 2,914,064 | 11/1959 | Sandelowsky | 128/145.6 |
| 2,972,345 | 2/1961 | Spigel | 128/145.6 |
| 3,094,274 | 6/1963 | Thompson | 415/125 |
| 3,120,228 | 2/1964 | Huxley | 128/30.2 |

FOREIGN PATENT DOCUMENTS 549005 10/1956 Italy .................................. 128/145.6

*Primary Examiner*—Henry J. Recla
*Attorney, Agent, or Firm*—Jerry W. Berkstresser

[57] ABSTRACT

The present invention relates to improvements in the portable, positive-pressure artificial respiration apparatus and, more particularly, to improvements in the air passageway systems of such apparatus by using a dual control valve.

9 Claims, 14 Drawing Figures

Cycle Time — Selected for Patient

DUAL CONTROL VALVE FOR POSITIVE PRESSURE ARTIFICIAL RESPIRATION APPARATUS

Portable positive-pressure respirators will normally be operated by 110 volt AC power, such as is commonly available in a home. For back-up, as in the event of a power failure, a 12-volt storage battery may be used. Also, the respirators may be used by wheel chair patients, by mounting a storage battery in the wheel chair. This gives the patients freedom of movement, away from 110 volt outlets for as much as four to six hours at a time. These respirators produce cyclic pulses of air flow under positive pressure at a selected breathing rate to aid a patient in breathing during inspiration. Usually, the flow of pressurized air is taken in the patients mouth through a breathing tube or a tracheotomy tube. The following apparatus will be described thus, although it is to be recognized that the apparatus can also be used to effect expiration by directing the cyclic flow of pressurized air into an inflatable bladder under an abdominal belt.

Artificial respiration apparatus of this type is exemplified in the patents to Huxley III, U.S. Pat. No. 3,120,228 and Thompson U.S. Pat. No. 3,094,274. To provide comparatively small, portable units, the conventional positive-pressure breathing units use a standard type of a cylindrical blower powered by an electrical motor which, as mentioned, will run by a household 110 volt AC power source or by a storage battery. Normal operation of the blower is to provide a continuous blast of air at a selected pressure. A portion of this air flow is directed through an exhaust tube for cooling purposes. Another portion of the air flow is directed through a cyclic valve to intermittently flow into the breathing tube during inspiration, and then to cut off during expiration.

It was recognized that the continuous air flow for cooling the blower motor and resistor was necessary although the blower had to maintain an air pressure somewhat greater than the maximum pressure through the breathing tube during inspiration.

The excess energy requirement resulting from this mode of operation is completely insignificant when the apparatus is operating on a regular 110 volt power supply. Thus, the general smooth and reliable operation of these units make the energy requirement for operation a secondary factor in their design. However, many patients realize that they can use the breathing apparatus with a storage battery, usually mounted in a wheel chair or a cart, in order to provide a freedom of movement not otherwise possible. The result is a growing demand, for this and other reasons, for positive pressure breathing apparatus which can operate with a storage battery for long periods of time before the battery becomes discharged. With conventional breathing units, a fully charged storage battery will provide about four to six hours of service, and an increase in this time period to at least eight hours, is desired.

With the foregoing and other considerations in view, the present invention was conceived and developed, and the invention comprises in essence: a modification of the valving system in the apparatus which cyclically directs air flow to the patient, to cyclically and intermittently cut off the exhaust flow during the inspiration cycle of breathing. It was discovered that with the arrangement hereafter described as a preferred embodiment of the invention, the resulting power input to the apparatus could be decreased, by reducing the exhaust flow pressure without reducing the inspiration breathing pressure. This meant that a storage battery, which could be used only for about four to six hours in a conventional unit would last for eight hours or longer in the improved unit.

It follows that the objects of the present invention are to provide a novel and improved valving system for a positive pressure artificial respiration apparatus which: (a) provides for accurate regulation of air at a selected pressure during the inspiration cycle of breathing; (b) reduces the pressure in the blower without adversely affecting the performance of the unit; (c) significantly reduces the power and energy required to operate the apparatus and; (d) is a simple, neat and reliable apparatus, easily installed in a conventional unit without disturbing or changing the arrangement of other components within the apparatus.

With the foregoing and other objects in view, all of which more fully hereafter appear, my invention comprises certain constructions, combinations and arrangements of parts and elements as hereinafter described, defined in the appended claims and illustrated in the accompanying drawings in which:

Figure 1:
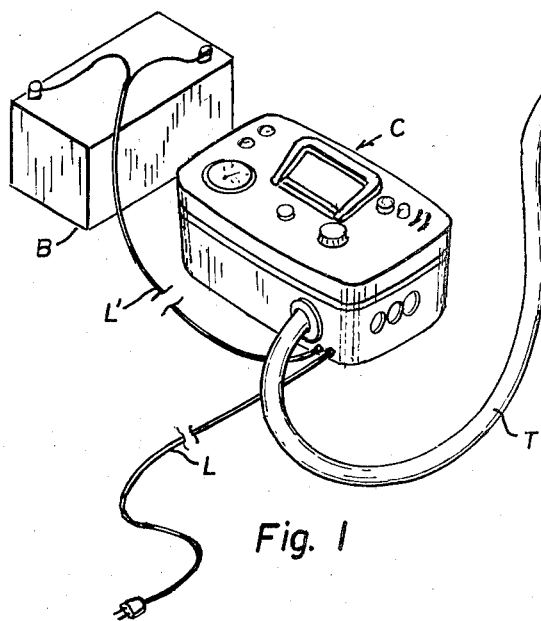
FIG. 1 is a perspective view of a portable positive pressure breathing unit having an electrical lead for connection with a 100-volt power source, an electrical lead for connection with a storage battery, and a breathing tube with a mouthpiece at its end.

Referring more particularly to the drawing, FIG. 1 illustrates a portable, positive-pressure breathing apparatus which includes a case C having an air blower and other operative components within it and controls and gages on its lid and sidewalls. An electrical lead L extends from this case C for normal use with a 110 volt A.C. power course, and a second electrical lead L' extends from the case for connection with a battery B for emergency and portage uses when the 110 volt power source is not available. A breathing tube T extending from the case C and terminating as a mouthpiece M completes the apparatus.

Figure 2:
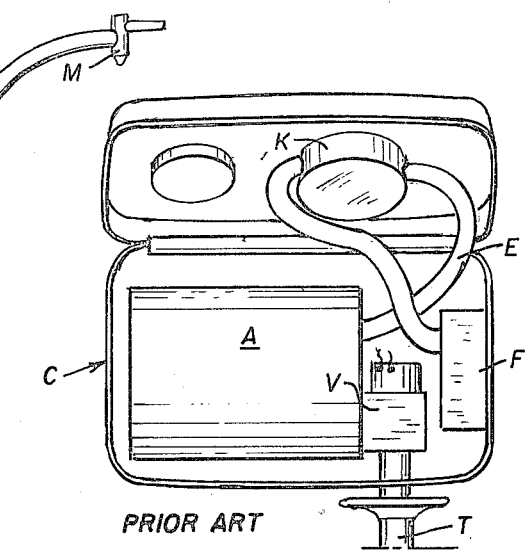
FIG. 2 is a plan view of a conventional unit, as shown at FIG. 1, but on an enlarged scale and with the lid lifted to show certain operative components within it.

FIG. 2 illustrates the case C of the breathing apparatus, with its lid lifted to show the interior of a conventional unit. However, many standard parts and electrical leads within this case are not shown, the figure illustrating only detail sufficient to show certain operative components with which the present invention is concerned. These components include an air blower A, a cyclic valve V connecting the air blower with the breathing tube T, an exhaust line E connecting with the air blower and extending thence to a resistor cooling can K and thence to an exhaust muffler F. All of these operative components are conventional and are shown in a conventional arrangement.

Figure 3:
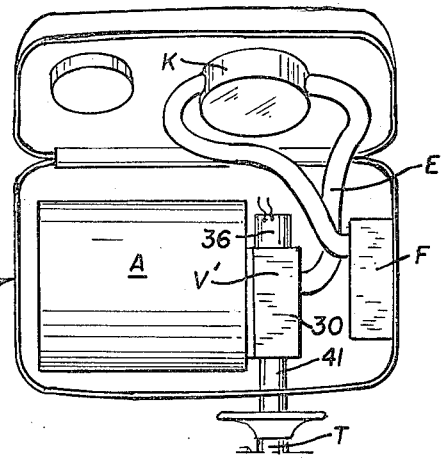
FIG. 3 is a plan view, similar to FIG. 2 but showing an improved unit with a dual cyclic valve replacing the conventional cyclic valve.

FIG. 3 illustrates the case C' with the improved dual cyclic valve V' in the breathing apparatus, to point out the general location and function of the valve V', all as hereinafter described in detail. The components within the case C' include the air blower A, the dual cyclic valve V' connecting with the air blower, the breathing tube T connecting with the dual cyclic valve and the exhaust line E also connecting with the dual cyclic valve to extend thence to a resistor cooling can K and thence to an exhaust muffler F. It is to be noted that the significant structural difference between this arrangement of components and the conventional arrangement, such as at FIG. 2, is that the exhaust line E is connected to the dual cyclic valve V' instead of being connected to the air blower A.

Figure 4:
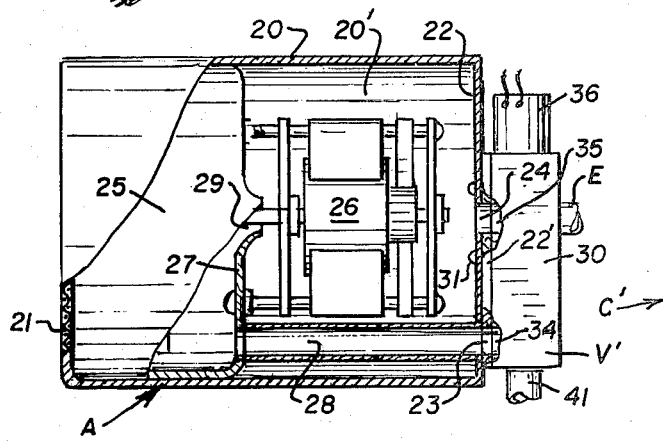
FIG. 4 is an enlarged view of the blower and dual cyclic valve within the unit shown at FIG. 3, and with portions broken away and in section to show parts otherwise hidden from view.

The construction of the air blower A and the basic arrangement of the dual cyclic valve V' connected to this air blower is best illustrated at FIG. 4. The blower A is contained within a cylindrical housing 20. A filter 21 is provided at the intake end of this housing and an end wall 22 closes its discharge end. A breathing tube discharge port 23 and an exhaust line discharge port 24 are located at this end wall. A cylindrical air turbine 25 snugly fits within the intake-end portion of the housing 20 with its intake adjacent to the filter 21. An electrical drive motor 26 is mounted in the motor chamber 20' adjacent to the discharge end of the housing 20 and its drive shaft is axially aligned with and connected to the shaft of the turbine 25. The turbine is formed with a discharge wall 27 whereon the motor is mounted, and this turbine discharges air through a tube 28 which extends from the wall 27, across the motor chamber 20 and connects with the breathing tube discharge port 23 in the end wall 22. A central opening 29 is provided in the discharge wall 27 through which the motor shaft extends to drive the blower. This opening 29 provides for a flow of air from the blower and into the motor chamber 20' of the housing 20 to discharge through the exhaust line discharge port 24.

It is to be noted that the proportions of the passageway and restrictions formed by the tube 28, the breathing tube discharge port 23, the exhaust line discharge port 24 and the valve V' are balanced in such a manner as to produce a maximum air pressure of 30 to 40 centimeters of water in the breathing tube T and in the motor chamber 20' when the blower is operating at selected normal design speeds. The variations of pressure in the breathing tube T and in the motor chamber 20' during the inspiration and expiration cycles of breathing which are obtained with this apparatus are shown at FIG. 5 and will be hereinafter further described.

Figure 5:
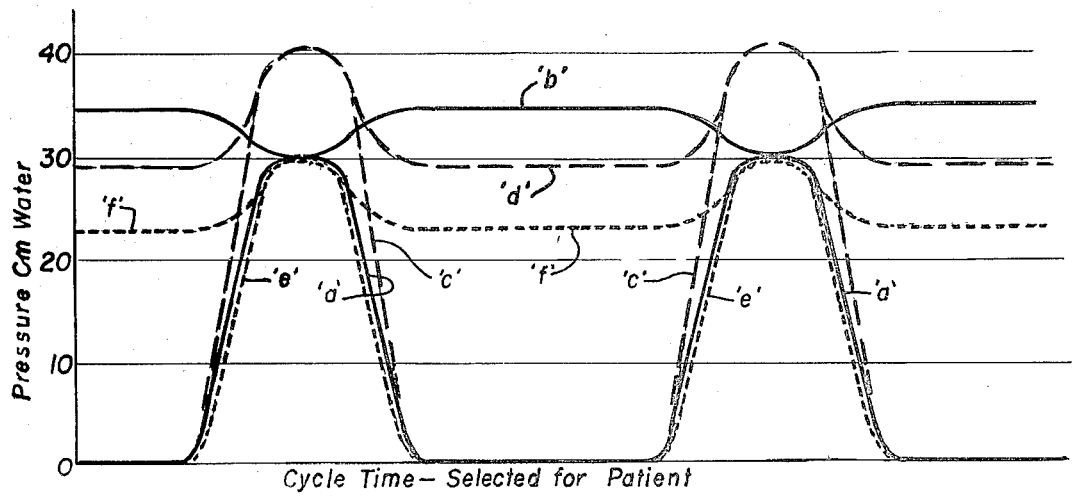
FIG. 5 is a pressure-time graph to illustrate and compare pressure variations during breathing within a conventional unit and within the improved unit.
Figure 6:
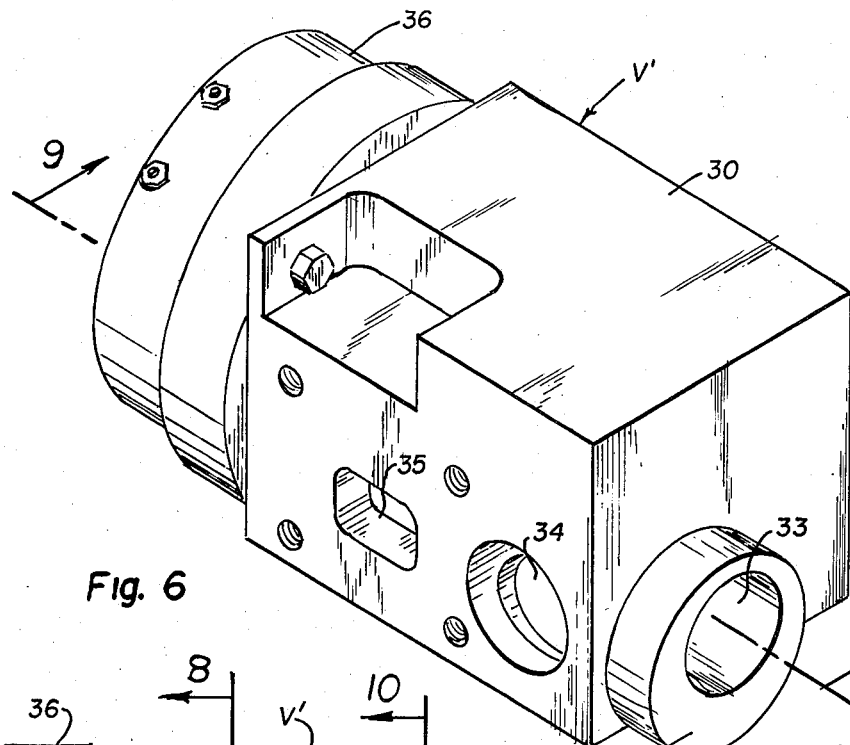
FIG. 6 is an isometric view of the dual cyclic valve per se, on a further enlarged scale, and with the driving motor mounted thereon.

The dual cyclic valve V' which cyclically controls flow in the breathing tube as in the manner shown at FIG. 5 includes a first port means to open and close the passageway to the breathing tube T and a second port means to open and close the passageway to the exhaust line E. The two port means may be operated by a common driving means, or if they are operated by separate driving means, such driving means must be interlinked. Also, the valves may be physically interlinked. Several different types of valves can be adopted for use with the dual cyclic valve V' and while the preferred type is a rotating spool valve, which will be hereinafter described in detail, it must be recognized that other types of valves can be used. This preferred spool valve will be operated by a rotor motor. Another type, which could be made fully equivalent, would be a dual reciprocating spool valve. This reciprocating valve can be operated by solenoids or by other plunger means. Such will not be herein described in detail since reciprocating spool valves are well known in the art and it is only a matter of timing and proportioning of the ports to function in the desired manner. The same arguments can be directed to other well known types of valves and driving means.

Figure 11:
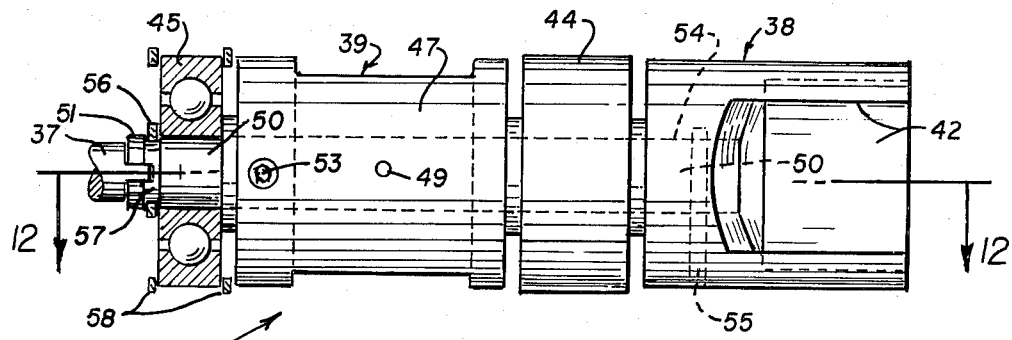
FIG. 11 is a side elevational view of the rotatable spool of the dual cyclic valve, on a further enlarged scale, with a bearing and lock rings shown in section and with a fragment of the motor drive shaft being connected thereto.
Figures 13, 14:
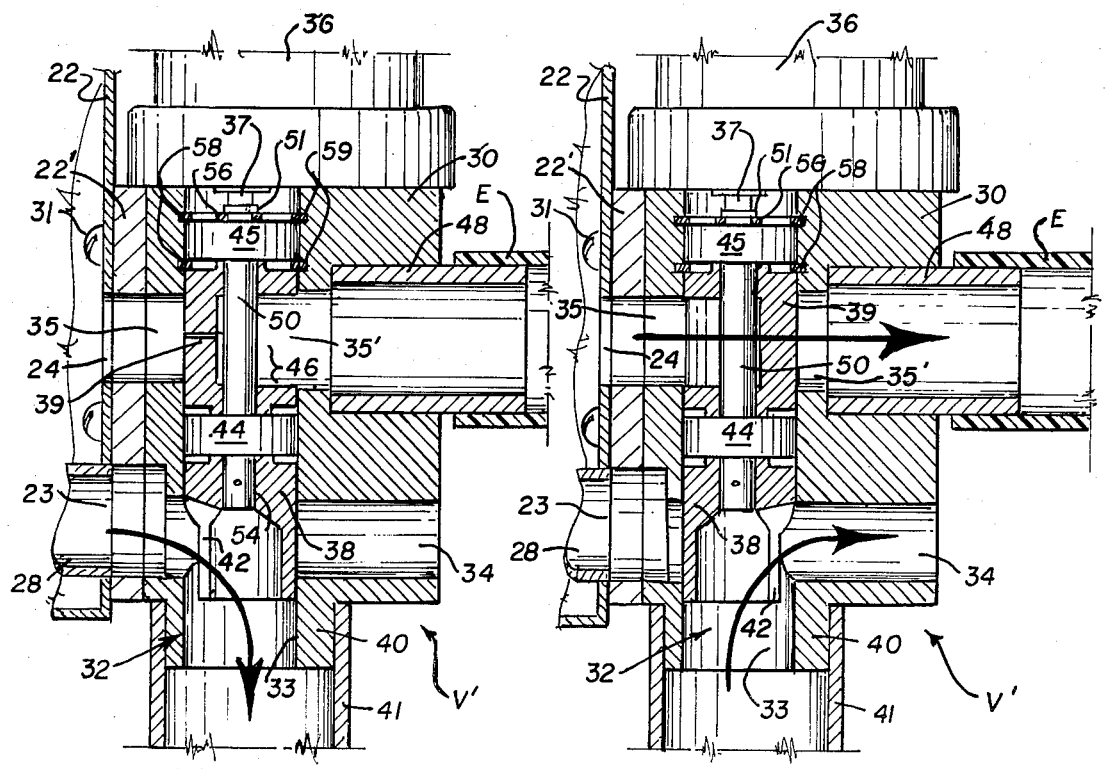
FIG. 13 is a sectional view as taken from the indicated line 13—13 at FIG. 9. but showing the valve connected to the blower, with the rotating spool shifted to a position for inspiration, and with an arrow indicating the direction of air flow.
FIG. 14 is a sectional view similar to FIG. 13 but with the spool shifted to a position for expiration and with arrows indicating the direction of air flow.

The dual cyclic valve V' is formed within a rectangular box-like body 30 and it is preferably mounted to the housing end wall 22 as with machine screws 31 as shown at FIGS. 4, 13 and 14. A spacer washer 22' between the wall 22 and the valve body may be used for clearance of parts. A cylindrical, compound spool 32 is mounted in a longitudinal cylindrical chamber 33 in the body 30. The chamber 33 is intercepted by transverse passageways 34 and 35. The passageway 34, a breathing passageway, registers with the breathing tube discharge port 23 and the passageway 35, a discharge passageway, registers with the exhaust line discharge port 24, as shown at FIGS. 4 and 13. A rate motor 36, a synchronous type motor, has its speed selectively controlled by conventional electronic components to provide any desired breathing rate. This motor 36 is mounted at that end of the body 30 which is opposite to the connection with the breathing tube T. The drive shaft 37 of the rate motor connects with the end of the spool 32 within the chamber as best shown at FIGS. 9, 11 and 13.

To function as a dual valve, the spool 32 is formed with two valve segments, an outer end segment 38 which intercepts the breathing passageway 34 and an inner discharge segment 39 which intercepts the discharge passageway 35. The outer end segment 38 is cup-shapoed with the open cupped end facing the exit end of the chamber 33. A tubular stub 40 outstands from the end wall of the body 30 to define the exit end of the chamber 33 and a short tube 41 is connected to this stub to extend through the case C' and connect with the breathing tube T as best shown at FIGS. 3 and 9.

Figure 10:
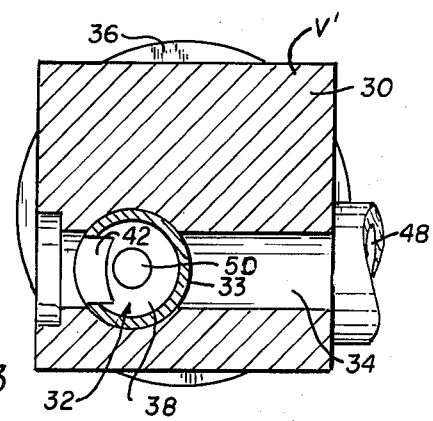
FIG. 10 is a transverse sectional view, as taken from the indicated line 10—10 at FIG. 7.

The cup-shaped end segment 38 fills the cylindrical chamber wall 33 to close off the passageway 34, however, a slot 42 in the segment 38 will register with the passageway 34 as the spool 32 rotates to cyclically provide an air flow from supply tube 28, into passageway 34, through the chamber 33 and thence through the breathing tube T as best shown at FIGS. 10 and 13. Such air flow defines the inspiration cycle of the apparatus. As rotation continues, the air flow from the supply tube 28 is cut off and as the slot 42 moves to the opposite open side of the passageway 34, the air under pressure in the breathing tube may be exhausted to the atmosphere from the passageway 34 as best shown at FIG. 14. This reverse air flow defines the expiration cycle of breathing and while expiration may be from, or adjacent to, the patient's mouth to stop air movement in the breathing tube, some reverse blow and discharge of air from the passageway 34 can occur.

Figure 9:
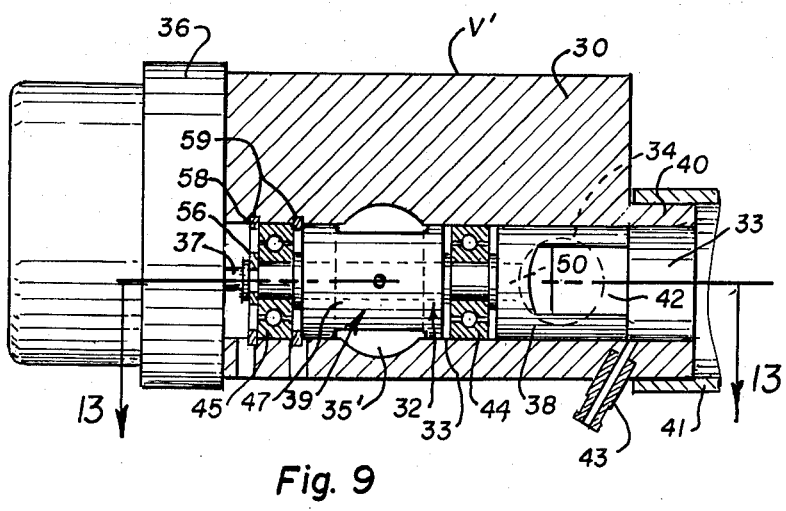
FIG. 9 is a longitudinal sectional view, as taken from the indicated line 9—9 at FIG. 6, but with a fragment of a connective line being attached.

To complete this portion of the valve a piezometer 43 is provided in the wall of chamber 33 adjacent to the end of the segment 38 as best shown at FIG. 9. This piezometer 43 connects with a pressure gauge line, not shown, for measurement of static air pressure in the breathing tube T.

Figures 7, 8:
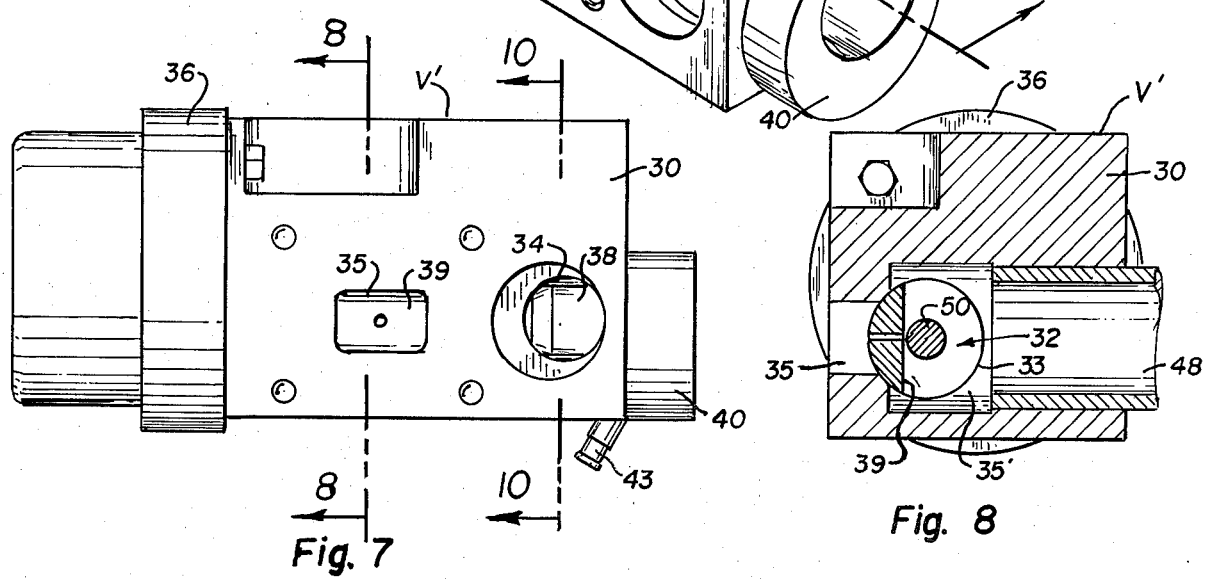
FIG. 7 is a side elevational view of the dual cyclic valve and drive motor at a scale comparable to that of FIG. 6, as from the intake side of the valve.
FIG. 8 is a transverse sectional view, as taken from the indicated line 8—8 at FIG. 7.

The inner segment 39 of the spool 32 is located in that portion of the chamber 33 which is intercepted by the discharge passageway 35 connecting with opening 24 as best shown at FIGS. 13 and 14. It is separated from the outer end segment 38 by a bearing race 44, and from the rate-motor drive shaft 37 by a bearing race 45. This inner segment is cut away at one side by a notch 46 leaving a cylindrical sector 47 at one side which rotates to close the passageway 35 in a cyclic manner as best shown at FIG. 8. This passageway 35 is enlarged at its exit side as at 35', the side opposite opening 24, for free movement of air about the sector when the sector does not close the passageway. A tube stub 48 is fitted into this opening for connection with the exhaust line E. It is to be noted that the sector 47 will be positioned to close exhaust passageway 35 during the inspiration cycle of the patient and to open the passageway during expiration cycle of the patient. As such the cylindrical face of the sector 47 is diametrically opposite to, or 180 degrees from the slot 42 of the outer segment 38 of the spool 32, as best shown at FIGS. 13 and 14. A small relief hole 49 may extend through the sector 47 of the inner segment 39 to permit a small air flow through the exhaust line in case the spool becomes stuck, thus preventing severe overheating of the motor 26 or the resistor in the can K. The same leakage is possible by providing a small clearance between the face of the sector 47 and the wall of the chamber 33.

Figure 12:
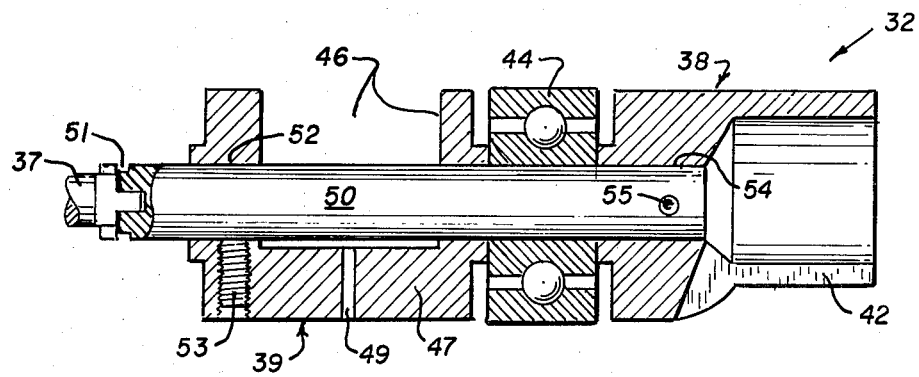
FIG. 12 is a sectional view as taken from the indicated line 12—12 at FIG. 11 but without the bearing and lock rings.

The construction of the spool 32 is best shown at FIGS. 11 and 12. A central shaft 50 carries the bearing races 44 and 45 with a slotted connective end 51 for connection with a tongue on the rate-motor drive shaft 37. The inner segment 39, having a central bore 52, is fitted upon this shaft 49 between the bearing races 44 and 45 and is secured in place by a set screw 53. The outer end of the shaft projects from the bearing 44 and is fitted in a socket 54 in the base of the cup-shaped outer end segment 32. It is secured in place by a lock pin 55 to complete this spool assembly. The bearing race 45, mounted on the shaft 50 adjacent to the end 51, is held in place upon the shaft by a lock ring 56 fitted into a slot 57 on the end of the shaft. The spool 32 is fitted in place in the chamber 33 by lock rings 58 at each side of the bearing race 45 which are held in place in annular slots 59 in the chamber 33, as shown in FIGS. 9, 13 and 14.

The advantages of operation of the positive pressure breathing apparatus with the improved valve 'V,' as compared with a conventional apparatus, (FIG. 3) are set forth by the pressure graphs at FIG. 5. The pressures shown in this graph are obtained by the piezometer 43 at the breathing tube and a similar piezometer, not shown, in the motor chamber 20'. That piezometer is not shown because it is not needed for operation of the apparatus but only for testing as now described. In a conventional unit where the exhaust flow is not restricted by a valve means, a typical cyclic pressure variation in the breathing tube T is shown by the solid-line curve 'a' while the pressure variation in the blower motor chamber 20' is shown by the solid line curve 'b.' The peak valve of curve 'a' is shown to be approximately 30 centimeters of water, a typical value for many patients, and is one important factor in selecting a proper breathing pattern for a patient. It is to be noted that the pressure in the blower motor chamber 20', curve 'b,' is necessarily greater than the maximum pressure delivered to the patient, the peak value of curve 'a,' and that the pressure curve 'b' drops a small amount, essentially to the curve 'a' peak during the inspiration cycle of breathing. An excessive use of energy in such an arrangement is suggested since the blower must continuously pump air at a pressure greater than the maximum pressure needed for inspiration, to provide a continuous flow through the exhaust line E to cool the motor and the resistor in the can K.

The dual cycle valve 'V' provides for an operation which, for the same power input to the motor, permits an increased peak pressure in the breathing tube during the inspiration cycle, the dashed curve 'c,' and a reduced pressure in the motor chamber, the dashed curve 'd.' When the inner segment 39 momentarily closes, the exhaust line E, the pressure in the motor chamber 20' rises to match the maximum pressure at the breathing tube T.

A more significant result is set forth by the dotted-line curves 'e' and 'f,' which are obtained by reducing the power input to the motor to a point where the maximum pressure of curve 'e' is essentially 30 centimeters of water, the same as that of curve 'a.' This reduction means a savings of power and is very significant when the breathing apparatus is being operated by a battery B, for it gives the patient a longer period of time when he is using the battery B, which is necessary in an emergency or when the patient is away from a 110-volt power source.

Several variables enter into designing a selected inspiration-expiration breathing curve. For example, the maximum pressures are established by the power input to the blower and the timing of the breathing cycles are controlled by the rate-motor 36. The manner in which air is supplied to the patient, as would be indicated by the shape of the inspiration surves 'a,' 'c' and 'e' of FIG. 5, can be varied by changing the shape or size of the passageways 34 and 35, the physical form of the slot 42 of spool segment 38 and, sector 47 of the spool segment 39. Such changes may also include changing the width of theeir relative positioning, as from the 180-degree diametrical position above described, to a different angular position. The effect of such changes to change the width and symmetry of the inspiration curve are easily determined by simple experiments, well within the skill of an artisan.

While I have now described my invention in considerable detail, it is obvious that others skilled in the art can devise and build alternate and equivalent constructions which are nevertheless within the spirit and scope of my invention. Hence, I desire that my protection be limited, not by the constructions illustrated and described but only by the proper scope of the appended claims.

What is claimed is:

1. In a positive-pressure artificial respiration apparatus, for aiding in inspiration and expiration cycles of breathing by a patient, of the type having a continuously-operating blower connected to a blower motor mounted in a motor chamber and having a first discharge path means from said blower to a first discharge port connected to a breathing tube and a second discharge path means from said blower through said motor chamber around said motor and to a second discharge port connected to an exhaust line, the improvement comprising:
    (a) a first cyclic valve means between the said first discharge port and the breathing tube to open to permit air flow from the blower and into the breathing tube and to close to stop such air flow;
    (b) a second cyclic valve means between the said second discharge port and the exhaust line to open to permit air flow from the blower and into the exhaust line and to close to stop such air flow; and
    (c) an interlinking drive means to cyclically drive the said first and second cyclic valve means in opposition to close the second cyclic valve means when the first cyclic valve means is open and to open the second cyclic valve means when the first cyclic valve means is closed.

2. The apparatus defined in claim 1, wherein:
said first cyclic valve means includes an exit means which is closed off when the valve means is open with air flowing from the blower and into the breathing tube, but which is open to the breathing tube when the valve means is closed to permit air in the breathing tube to reverse and flow from the exit means.

3. The apparatus defined in claim 1, wherein:
    (a) the said first and second cyclic valve means are operably linked together by a linkage; and
    (b) the drive means comprises a single rate motor connected with the linkage.

4. The apparatus defined in claim 3, wherein:
    (a) the said first and second cyclic valve means comprise first and second cylindrical spool segments, respectively, operably linked together upon a common shaft;
    (b) said spool segments are fitted into a common cylindrical chamber of a single valve body;
    (c) a first passageway through the valve body commencing at the said first discharge port, extending to the cylindrical chamber and extending thence to the breathing tube, and with the said first spool segment in the chamber intercepting this passageway;
    (d) a second passageway through the valve body commencing at the said second discharge port, extending to the cylindrical chamber and extending thence to the exhaust line, and with the said second spool segment in the chamber intercepting this passageway.

5. The apparatus defined in claim 4, wherein:
    (a) the rate motor rotates the spools to effect cyclic valve action with a single rotation for inspiration and expiration cycles of breathing;
    (b) the said first spool segment is located adjacent to one end of the valve body, with the cylindrical chamber extended to and exiting at this end of the body and with the breathing tube being connected to this end of the body at the chamber exit;
    (c) the said first spool segment is cup shaped, with the cup cavity facing the chamber exit, with the cylindrical wall of the spool segment closing the aforesaid first passageway; and
    (d) a slot in the wall of the spool to divert air flow from the passageway, into the chamber and thence into the breathing tube when spool rotation registers the slot with the intake portion of the passageway, at the side connecting with the said first discharge port of the blower, and to divert air flow from the breathing tube and to the atmosphere when the slot registers with the discharge portion of the passageway at the side of the passageway extended through the body and open to the atmosphere.

6. The apparatus defined in claim 5 wherein:
    (a) the said second spool segment is notched so that only an arcuate face portion of the segment will cover the intake portion of the said second discharge passageway, at the side connecting with the second said discharge port and the blower;
    (b) the discharge portion of said second passageway, at the side connecting with the exhaust line, is enlarged to be wider than the chamber whereby the arcuate face portion of the segment will not block this discharge portion of the passageway; and
    (c) said arcuate face portion covers the intake portion of said second discharge passageway when the slot of the aforesaid first spool segment registers with the intake portion of the aforesaid first passageway whereby to cut off exhaust flow during the inspiration cycle of breathing.

7. The apparatus defined in claim 6, wherein:
a clearance means is provided at the said arcuate face portion and the intake of the said second discharge passageway whereby to permit a small leakage flow of air to pass through the exhaust line when the second cyclic valve means normally closes the exhaust line.

8. The method for regulating the air flow in a positive-pressure artificial respiration apparatus, for aiding in inspiration and expiration cycles of breathing by a patient, of the type having a continuously-operating blower connected to a blower motor mounted in a motor chamber and having a first discharge path means from said blower to a first discharge port connected to a breathing tube and a second discharge path means from said blower through said motor chamber around said motor and to a second discharge port connected to an exhaust line and a valve means at each discharge port, including the steps of:
    (a) cyclically operating the valve means at the said first discharge port to open to permit air flow from the blower and into the breathing tube and to close to stop such air flow;
    (b) cyclically operating the valve means at the said second discharge port to open to permit air flow from the blower and into the exhaust line and to close to stop such air flow; and (c) regulating the aforesaid cyclic valve means operations to stop air flow into the exhaust line when air is flowing into the breathing tube and to permit air flow into the exhaust line when the air flow into the breathing tube is stopped.

9. The method defined in claim 8 including the further step of:

cyclically valving the passageway at the breathing tube to permit air to flow from the breathing tube and to the atmosphere when the air flow from the blower and into the breathing tube is stopped.

* * * * *